(12) United States Patent
Wieselblad

(10) Patent No.: US 8,372,042 B2
(45) Date of Patent: Feb. 12, 2013

(54) DOSE SETTING MECHANISM

(75) Inventor: Anders Wieselblad, Stockholm (SE)

(73) Assignee: SHL Group AB, Nacka Strand (SE)

( * ) Notice: Subject to any disclaimer, the term of this patent is extended or adjusted under 35 U.S.C. 154(b) by 0 days.

(21) Appl. No.: 13/203,305

(22) PCT Filed: Jul. 31, 2009

(86) PCT No.: PCT/EP2009/059963
§ 371 (c)(1),
(2), (4) Date: Aug. 25, 2011

(87) PCT Pub. No.: WO2010/097125
PCT Pub. Date: Sep. 2, 2010

(65) Prior Publication Data
US 2011/0313365 A1 Dec. 22, 2011

Related U.S. Application Data

(60) Provisional application No. 61/155,765, filed on Feb. 26, 2009.

(51) Int. Cl.
A61M 5/178 (2006.01)
A61M 29/00 (2006.01)
A61M 5/00 (2006.01)
(52) U.S. Cl. .............. 604/186; 604/97.02; 604/207
(58) Field of Classification Search .......... 604/95.01, 604/181, 186, 97.02–97.03, 207–211
See application file for complete search history.

(56) References Cited

U.S. PATENT DOCUMENTS 5,591,136 A 1/1997 Gabriel
2007/0233015 A1* 10/2007 Saiki .................. 604/207
2009/0293870 A1* 12/2009 Brunnberg et al. ...... 128/203.12

FOREIGN PATENT DOCUMENTS

EP 0373321 A1 6/1990
WO 01/72361 A1 10/2001
WO 02/20495 A2 4/2002

OTHER PUBLICATIONS

EPO, Intl Search Report in PCT/EP2009/059963, Feb. 25, 2010.
EPO, Written Opinion in PCT/EP2009/059963, Feb. 25, 2010.

* cited by examiner

Primary Examiner — Nicholas Lucchesi
Assistant Examiner — Rebecca E Eisenberg
(74) Attorney, Agent, or Firm — Potomac Patent Group PLLC

(57) ABSTRACT

A dose setting mechanism for a medicament delivery device includes a tubular housing having threads on its inner surface, a first window, a second window, and at least one surface opening; a tubular dose limiting member having a first thread segment on its outer circumference for the threads on the housing's inner surface, first indicia on its outer circumference, a stop surface, and equidistant protrusions on its outer circumference; a tubular dose setting member; and a removable lock member attached to the housing. The housing is coaxially arranged inside the dose limiting member and includes a second thread segment for the housing's threads, second indicia, and a dose setting knob protruding through the housing. The lock member includes at least one elongated rib on its inner circumferential surface for interacting with the protrusions for locking the dose limiting member in position when the lock member is attached to the housing.

4 Claims, 5 Drawing Sheets

DOSE SETTING MECHANISM

TECHNICAL AREA

The present invention relates to a dose setting mechanism to be used in medicament delivery devices.

BACKGROUND

There are many devices for delivery of medicament that have been developed for self-use, i.e., that the patient or other non-medically trained persons handles the device during medicament delivery. Such devices comprise inhalers, nebulizer and injectors. For many treatments, like asthma, diabetes, hormone growth, the patient has to receive doses on a regular basis and the advantage with such devices is that the patient can administer the delivery anywhere and is not bound to visit care facilities in order to receive medication.

The self-medication devices need to both reliable and easy to use for an untrained user. It is thus necessary that the risks of wrong handling of the device are minimized so that the user cannot receive wrong dose sizes.

A number of devices have the possibility of setting a certain dose size, which size depends on the actual patient and the treatment and where the device is capable of delivering a number of doses before the medicament in the device is finished. However for many patients and treatments the same dose size is to be set for every delivery. In these aspects it is also important that the dose cannot be set too high, which otherwise could cause serious consequences. Especially for children that are to self-administer medication, it is a safety aspect for the parents and the physician that the dose cannot be set too high.

Another problem of trying to limit the maximum allowable dose is with devices where the dose setting mechanism can be turned more than a full turn in order to set a dose. In devices of this kind it is difficult to arrange a dose stop by other means than a feature standing in the way for a rotation required to drive a piston so that a dose is provided, or relying on the spring in use to expand towards where a force no longer is exerted. In the first case one could be limited to doses that can be set within principally one turn of a dose knob.

SUMMARY

An aim of the present invention is to remedy the drawbacks of the state of the art devices and to provide a medicament delivery device that is safe regarding setting a dose to be administered.

This aim is obtained by the features of the independent patent claim. Preferable embodiments of the invention form the subject of the dependent patent claims.

According to an aspect of the invention, a dose setting mechanism intended to be used in a medicament delivery device, comprising an elongated tubular distal housing having opposite distal and proximal ends, wherein said distal housing comprises threads on its inner surface, a first window, a second window, and at least one opening on its elongated surface; a tubular dose limiting member having opposite distal and proximal ends, wherein said dose limiting member comprises a first thread segment on its outer circumference surface at its proximal end intended to cooperate with corresponding threads on the inner surface of the distal housing, first indicia on its outer circumferential surface, a stop surface at its proximal end, and a number of protrusions arranged equidistant to each other along the circumference on the outer surface at its distal end; a tubular dose setting member having opposite distal and proximal ends, wherein said dose setting member is coaxially arranged inside the dose limiting member and comprises a second thread segment having and end surface on its outer circumferential surface at its proximal end intended to cooperate with the threads of the distal housing, second indicia on its outer circumferential, and a dose setting knob protruding through the distal end of the distal housing; and a removable lock member attached to the distal housing, wherein said lock member comprises at least one elongated rib on its inner circumferential surface which is intended to interact with the protrusions of the dose limiting member for locking the dose limiting member in a certain position when the lock member is attached to the distal housing.

According to another aspect of the invention, the dose limiting member is arranged to be rotated and moved axially until an appropriate indicia is shown in the first window due to cooperation between the first thread segment and the threads on the distal housing by a manual actuation on the protrusions when the removable lock member is removed from the distal housing.

According to a further aspect of the invention, the dose setting member is arranged to be rotated by the dose setting knob and moved axially due to cooperation between the second thread segment and the threads on the distal housing until the end surface of the dose setting member abuts the stop surface of the dose limiting member, thereby preventing further movement of the dose setting member.

According to yet another aspect of the invention, the dose limiting member may be positioned in relation to the dose setting member such that the latter is capable of being turned more than 360° in order to set a prescribed dose, previously set by adjusting the dose limiting member.

An advantage of the present invention is that the stop surface of the dose limiting member may be moved to a certain position by the threaded rotation, which position corresponds to a prescribed dose quantity, where it is locked, and that the end surface of the dose setting member is abutting the stop surface of the dose limiting member when moved to the position which provides delivery of the prescribed dose, whereby the stop surface effectively stops further movement of the dose setting member.

It is thus not possible to set a larger dose than what has been preset by a physician or another trained person if the dose locking member is locked to a position corresponding to the set dose. Also with this invention it is possible to allow for the distinct feature of a dose stop also when desired dose setting ranges exceed one full turn of a dose knob to set a dose.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION

Figure 1A:
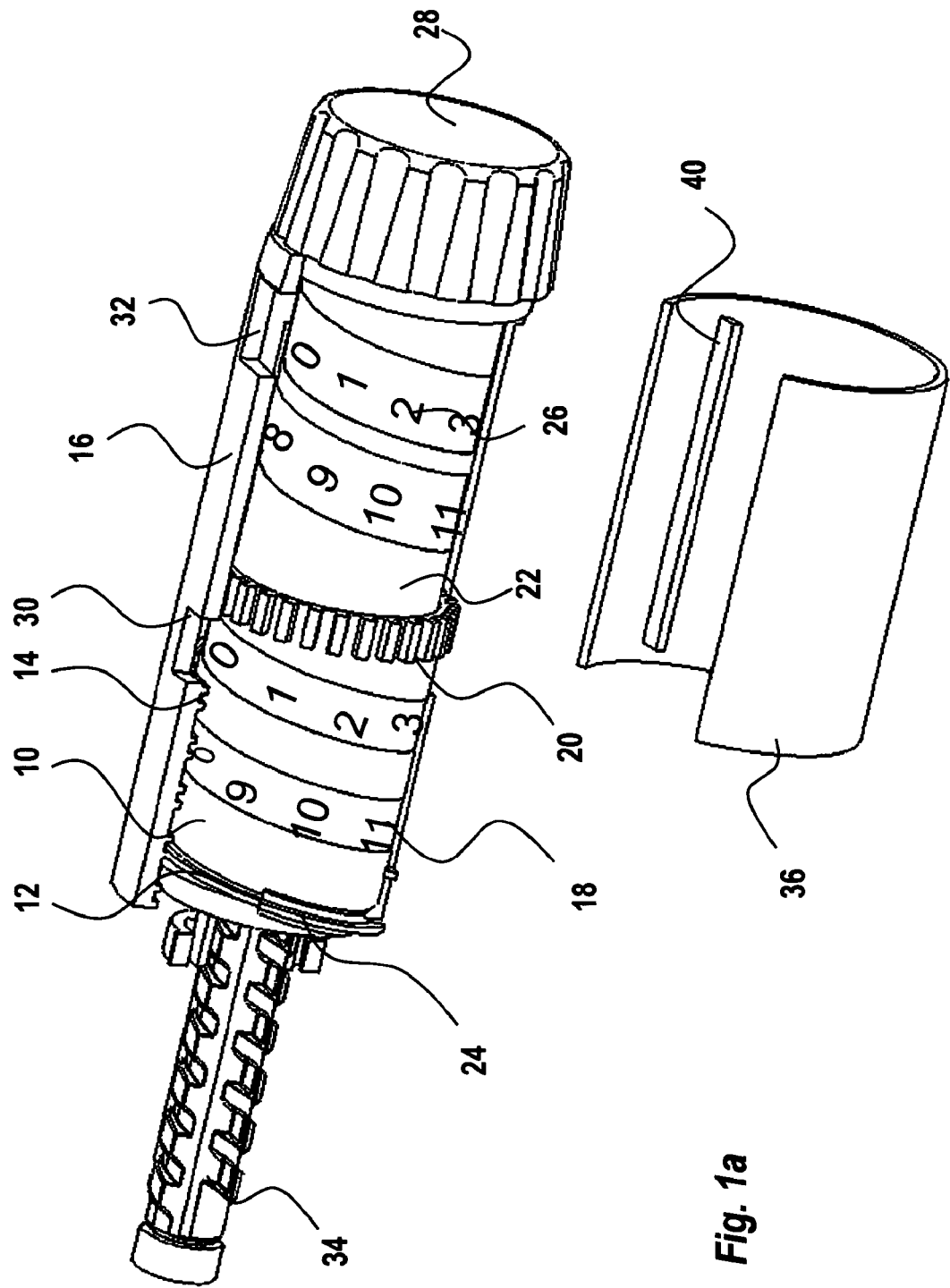
FIG. 1a shows a perspective view of the dose setting mechanism in an initial state with a part of a distal housing removed for clarity.

In the present application, when the term "distal part/end" is used, this refers to the part/end of the medicament delivery device, or the parts/ends of the members thereof, which under use of the device is located the furthest away from the delivery site of the patient. Correspondingly, when the term "proximal part/end" is used, this refers to the part/end of the device, or the parts/ends of the members thereof, which under use of the device is located closest to the delivery site of the patient.

The dose setting mechanism according to the present invention shown in the drawings comprises:

an elongated tubular distal housing 16 having opposite distal and proximal ends, wherein said distal housing comprises threads 14 on its inner surface, a first window 30, a second window 32 and at least one opening 38 on its elongated surface;

a tubular dose limiting member 10 having opposite distal and proximal ends, wherein said dose limiting member comprises a first thread segment 12 on its outer circumference surface at its proximal end intended to cooperate with corresponding threads 14 on the inner surface of the distal housing, first indicia 18 such as numbers, arranged in rows in a spiral pattern on its outer circumferential surface, a stop surface 42 at its proximal end, and a number of protrusions 20 arranged equidistant to each other along the circumference on the outer surface at its distal end;

a tubular dose setting member 22 having opposite distal and proximal ends, wherein said dose setting member is coaxially arranged inside the dose limiting member and comprising a second thread segment 24 having and end surface 44 on its outer circumferential surface at its proximal end, wherein said second thread segment is intended to cooperate with the threads 14 of the distal housing, second indicia 26 such as numbers, arranged in rows in a spiral pattern on its outer circumferential, and a dose setting knob 28 protruding through the distal end of the distal housing; and a removable lock member 36 attached to the distal housing, wherein said lock member comprises at least one elongated rib 40 on its inner circumferential surface which is intended to interact with the protrusions 20 of the dose limiting member for locking the dose limiting member in a certain position when the lock member is attached to the distal housing.

Figure 1B:
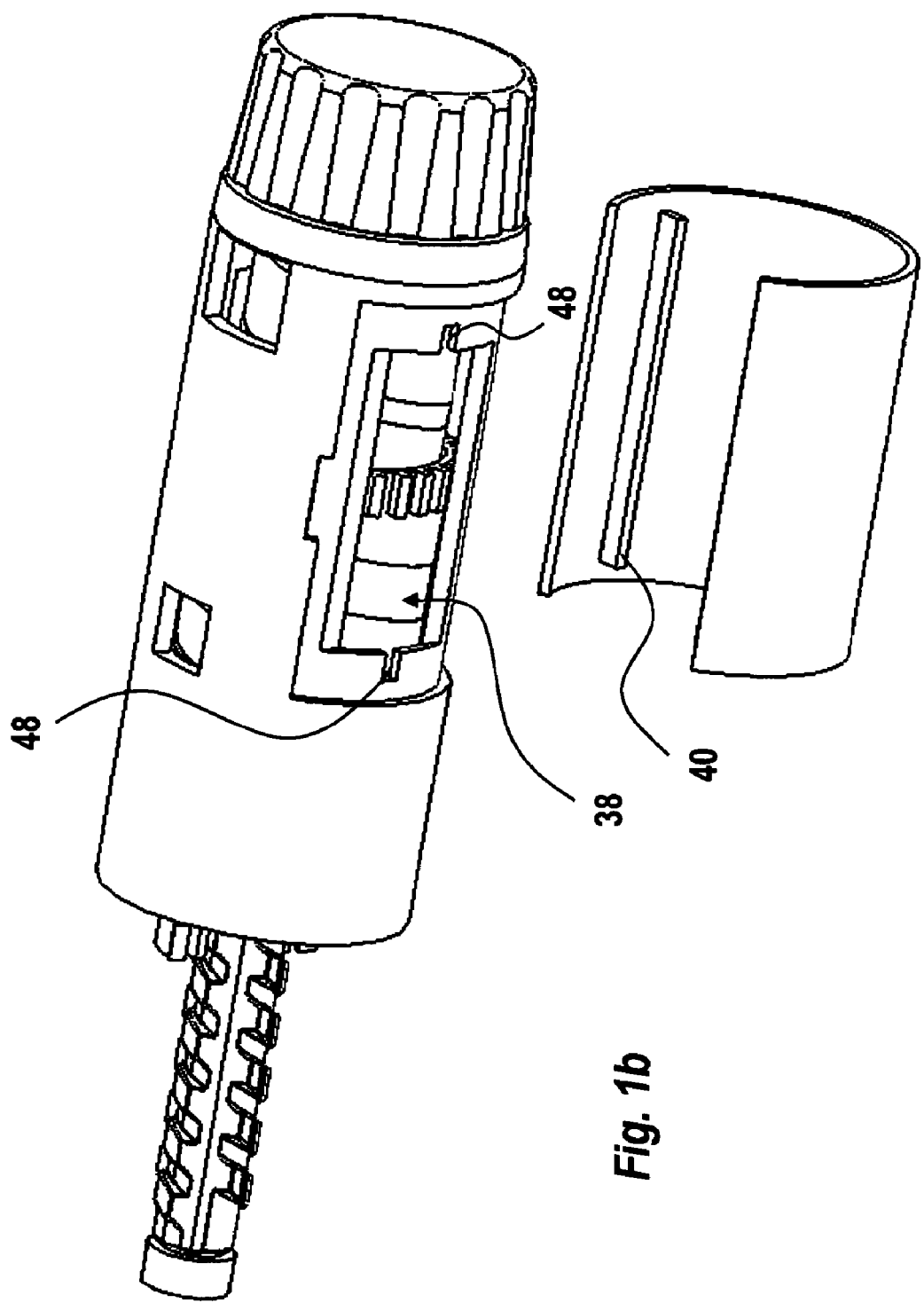
FIG. 1b shows a perspective view according to FIG. 1a with the distal housing intact.

Inside the dose setting member are arranged a driving mechanism (not shown) and a threaded plunger rod 34. The removable lock member 36 in the form of a lid forms a part of the distal housing and is arranged to be positioned over the at least one opening 38, FIG. 1b, on the elongated circumferential surface of the distal housing 16. The dose setting mechanism is intended to function as follows. When the device and the mechanism is in an initial state, as shown in FIG. 1a, both the dose limiting member 10 and the dose setting member 22 are positioned at the foremost proximal position. This position is limited for the dose setting member when the dose setting knob 28 abuts the distal end of the distal housing 16. This position is limited for the dose limiting member 10 by the stop surface 42 which is a cut-out at the proximal end of the dose limiting member, when said cut-out is abutting the end surface 44 of the second thread segment on the dose setting member. Further, in this position, the second thread segment 24 of the dose setting member 22 is aligned with the first thread segment 12 of the dose limiting member 10, as seen in FIG. 1a, where a part of the distal housing has been removed for clarity.

Figure 2:
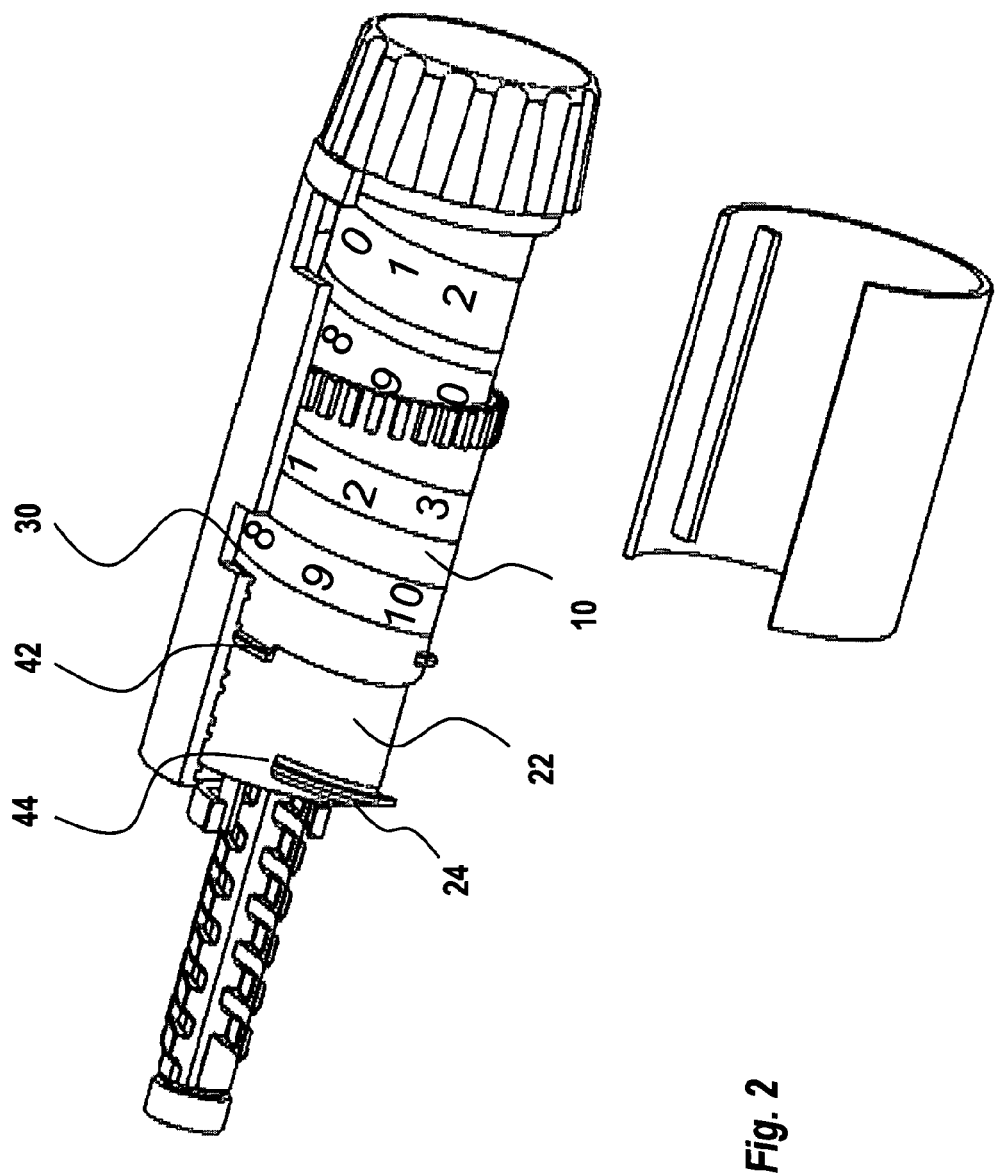
FIG. 2 shows a perspective view when a dose limiting member has been moved.
Figure 3:
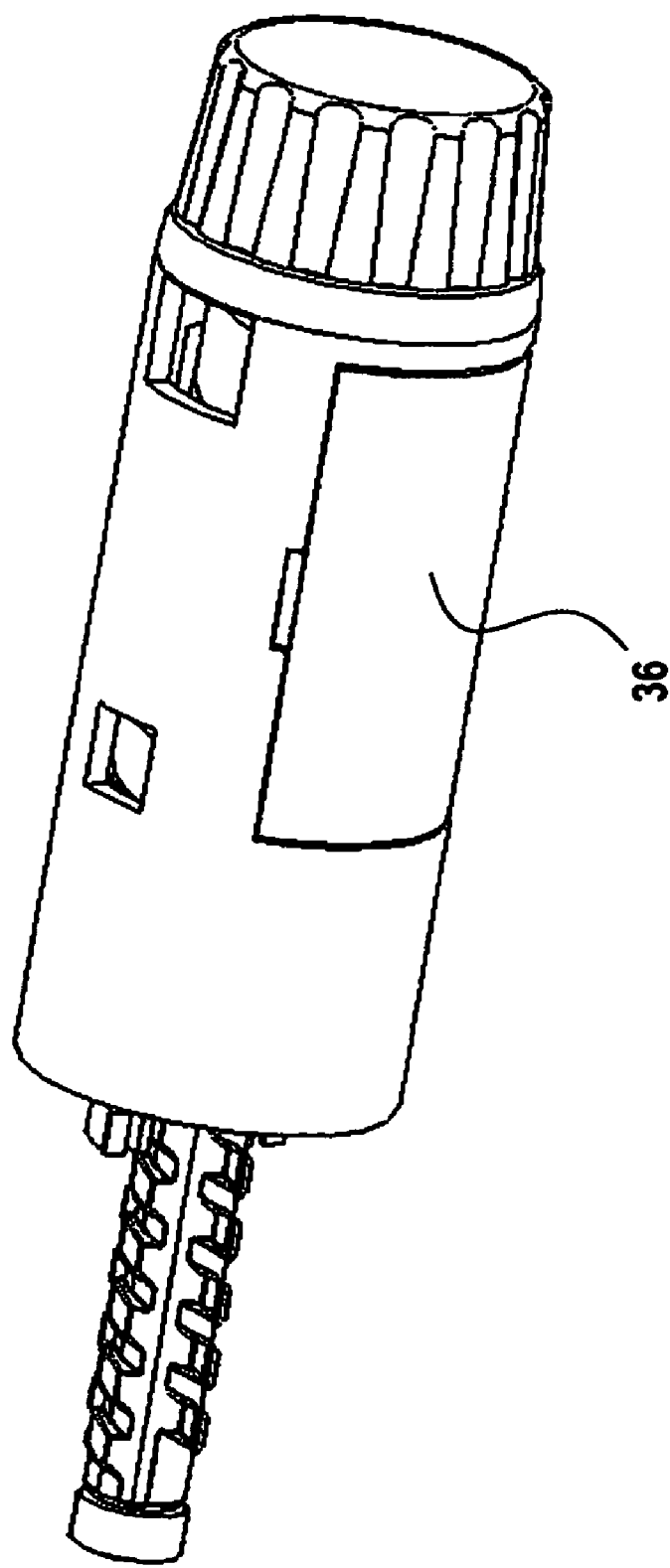
FIG. 3 shows the view of FIG. 2, when the dose limiting member has been locked.

When the device is to be activated for use, the lid 36 is removed from the distal housing, whereby the at least one opening 38 is visible, through which the protrusions 20 of the dose limiting member are accessible. The dose limiting member 10 can now be operated, preferably done by a physician or parent who has information regarding the dose quantity to be delivered to the actual patient. The dose limiting member is manually rotated via the at least one opening 38 and with the help of the protrusions 20. Due to the rotation and the cooperation between the first thread segment 12 on the dose limiting member 10 and the threads 14 of the distal housing 16, the dose limiting member 10 is rotationally moved towards the distal direction of the device. During the rotation, different first indicia 18 are displayed in the window 30, for example different dose sizes. The dose limiting member 10 is thus rotated until the prescribed dose size is visible in the window 30, FIG. 2. When the prescribed dose size is visible through the window 30, the dose limiting member 10 is locked by attaching the lid 36 to the distal housing 16 whereby the at least one elongated rib 40 is positioned between two adjacent protrusions 20 on the dose limiting member 10. The at least one rib also is fitted into at least one oppositely positioned cut-out 48 on the edge of the at least one opening 38, FIG. 1b. The dose limiting member is now locked and cannot be moved unless the lid is again removed. The device is thus ready for use, FIG. 3.

Figure 4:
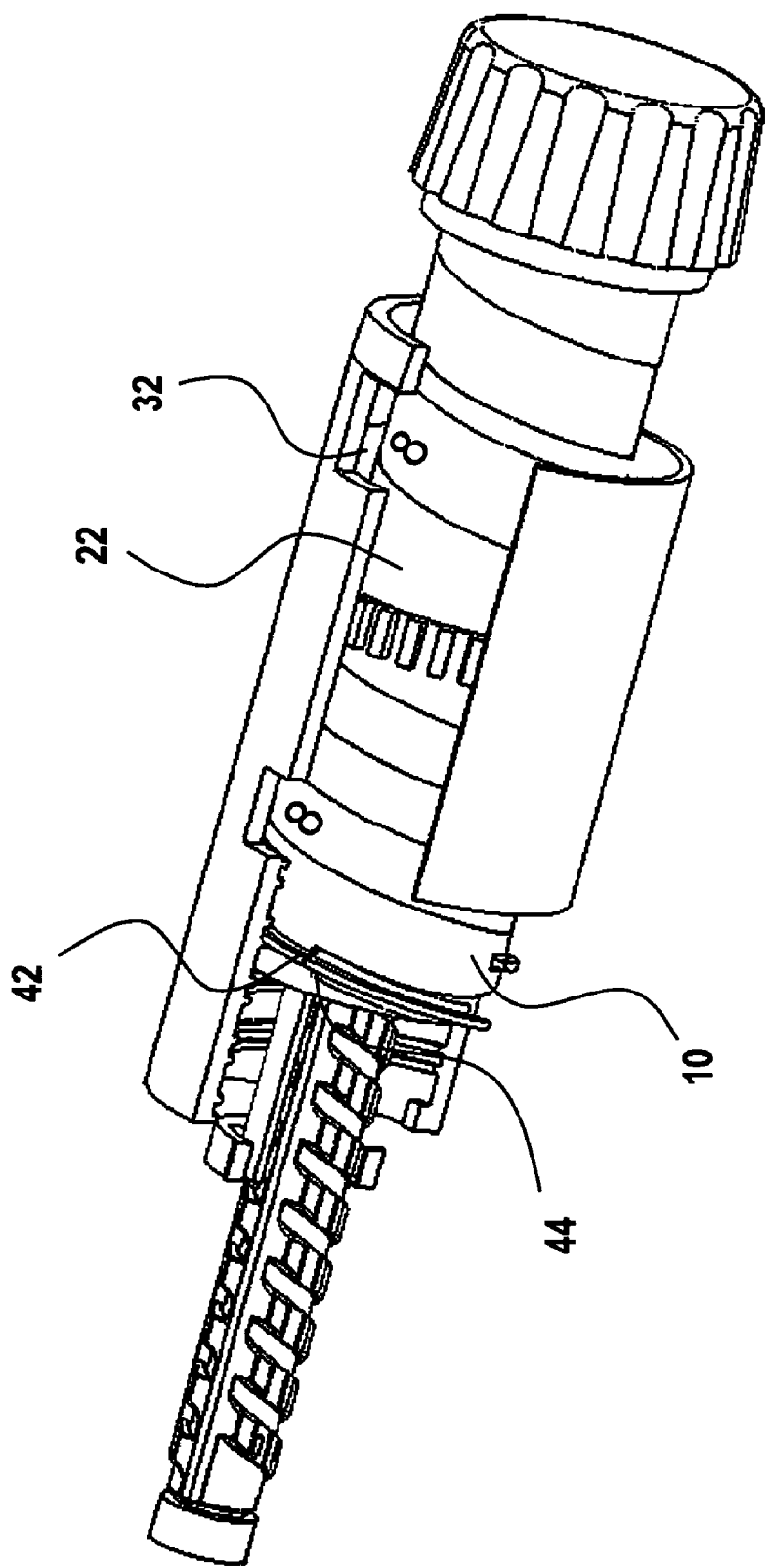
FIG. 4 shows a perspective view when a dose has been set.

When the patient or user is to administer a dose, the dose knob 28 is turned. This causes the dose setting member 22 to rotate and thus to move towards the distal direction of the device due to the second thread segment 24 of the dose setting member 22 cooperating with the threads 14 of the distal housing. During rotation, the second indicia 26 on the dose setting member 22 are shown through the window 32. The patient thus rotates the dose setting knob 28 until the prescribed dose quantity is displayed in the window 32, FIG. 4, whereby the device is ready for further medicament delivery actions such as e.g. penetration and injection when the device is an injector. Such latter steps or actions will not be described in detail since they do not form part of the invention. However, these steps may be performed manually as well as automatically, as is clearly apparent to the person skilled in the art.

However, should the user try to set a larger dose than the prescribed and preset dose size, this is prevented by the stop surface 42 of the dose limiting member 10. When the dose setting member 22 has reached the preset dose size, the end surface 44 of the second thread segment on the dose setting member and the stop surface 42 of the dose limiting member 10 are abutting each other, thereby stopping further movement of the dose setting member 22. During the subsequent delivery step, the dose setting member 22 is rotated and moved back to its initial position due to an appropriate connection between the plunger rod, the driving mechanism and the dose setting member 22. The device is now ready for the subsequent dose setting and dose delivery.

Also as is apparent from the above description of an embodiment the dose limiting function is valid also for doses that require more than a full turn, i.e. more than 360° rotation of the dose setting member.

It is to be understood that the embodiments described above and shown in the drawings only are to be regarded as non-limiting examples of the invention and that it may be modified in many ways within the scope of the patent claims.

The invention claimed is:

1. A dose setting mechanism for a medicament delivery device, comprising:
    an elongated tubular distal housing having opposite distal and proximal ends, wherein the distal housing comprises:
        threads on an inner surface of the distal housing; and
        a first window, a second window, and at least one opening on the distal housing's elongated surface;

a tubular dose limiting member having opposite distal and proximal ends, wherein the dose limiting member comprises:
- a first thread segment on an outer circumferential surface at the proximal end configured to cooperate with the threads on the inner surface of the distal housing;
- first indicia on the outer circumferential surface;
- a stop surface at the proximal end; and
- a number of protrusions arranged equidistant to each other along an outer circumferential surface at the distal end;

a tubular dose setting member having opposite distal and proximal ends and being coaxially arranged inside the dose limiting member, wherein the dose setting member comprises:
- a second thread segment having an end surface on an outer circumferential surface at the proximal end configured to cooperate with the threads on the distal housing;
- second indicia on the outer circumferential surface; and
- a dose setting knob protruding through the distal end of the distal housing; and a removable lock member attached to the distal housing, wherein the lock member comprises at least one elongated rib on its inner circumferential surface configured to interact with the protrusions of the dose limiting member for locking the dose limiting member in a certain position when the lock member is attached to the distal housing.

2. The mechanism of claim 1, wherein the dose limiting member is arranged to be rotated and moved axially until an appropriate indicia is shown in the first window due to cooperation between the first thread segment and the threads on the distal housing by a manual actuation on the protrusions when the removable lock member is removed from the distal housing.

3. The mechanism of claim 1, wherein the dose setting member is arranged to be rotated by the dose setting knob and moved axially due to cooperation between the second thread segment and the threads on the distal housing until the end surface of the dose setting member abuts the stop surface of the dose limiting member, thereby preventing further movement of the dose setting member.

4. The mechanism of claim 1, wherein the dose limiting member is configured to be positioned in relation to the dose setting member such that the latter is turnable by more than 360° order to set a prescribed dose, previously set by adjusting the dose limiting member.

* * * * *